United States Patent
Huang et al.

(10) Patent No.: US 11,872,445 B2
(45) Date of Patent: Jan. 16, 2024

(54) FITNESS MANAGEMENT METHOD, DEVICE, AND COMPUTER READABLE STORAGE MEDIUM

(71) Applicant: SHENZHEN SKYWORTH-RGB ELECTRONIC CO., LTD., Shenzhen (CN)

(72) Inventors: Yonglong Huang, Shenzhen (CN); Xian Wang, Shenzhen (CN)

(73) Assignee: SHENZHEN SKYWORTH-RGB ELECTRONIC CO., LTD., Shenzhen (CN)

( * ) Notice: Subject to any disclaimer, the term of this patent is extended or adjusted under 35 U.S.C. 154(b) by 697 days.

(21) Appl. No.: 17/042,159

(22) PCT Filed: Mar. 28, 2019

(86) PCT No.: PCT/CN2019/079992
§ 371 (c)(1),
(2) Date: Sep. 27, 2020

(87) PCT Pub. No.: WO2020/133765
PCT Pub. Date: Jul. 2, 2020

(65) Prior Publication Data
US 2021/0016136 A1 Jan. 21, 2021

(30) Foreign Application Priority Data
Dec. 27, 2018 (CN) .......................... 201811620014.8

(51) Int. Cl.
*A63B 24/00* (2006.01)
*G16H 20/30* (2018.01)
(Continued)

(52) U.S. Cl.
CPC ...... *A63B 24/0062* (2013.01); *A63B 24/0075* (2013.01); *A63B 71/0622* (2013.01);
(Continued)

(58) Field of Classification Search
CPC ............ A63B 24/0062; A63B 24/0075; A63B 71/0622; A63B 2024/0065; G16H 20/30;
(Continued)

(56) References Cited

U.S. PATENT DOCUMENTS 10,300,334 B1 * 5/2019 Chuang ................. G16H 50/30
2016/0151674 A1 * 6/2016 Rauhala ............. G06Q 30/0269
434/247

(Continued)

FOREIGN PATENT DOCUMENTS

CN 103500266 A 1/2014
CN 105678064 A 6/2016
(Continued)

OTHER PUBLICATIONS

Office Action in counterpart Indian Patent Application No. 202017048132, dated Sep. 15, 2021.
(Continued)

*Primary Examiner* — Sundhara M Ganesan
(74) *Attorney, Agent, or Firm* — Westbridge IP LLC

(57) ABSTRACT

A fitness management method, a fitness management device, and a computer readable storage medium are provided. The method comprises the following operations: acquiring a health evaluation result and health planning information corresponding to a first user account currently logged in; generating a fitness project on the basis of the health evaluation result and the health planning information; determining whether a smart terminal is currently connected to a data network; if so, determining whether there is a target network fitness application matching the fitness project among the network fitness applications currently installed on the smart terminal; and if so, displaying a first startup selection interface of the target network fitness application.

15 Claims, 4 Drawing Sheets

(51) Int. Cl.
  *G16H 50/30* (2018.01)
  *G16H 50/20* (2018.01)
  *A63B 71/06* (2006.01)

(52) U.S. Cl.
  CPC ............ *G16H 20/30* (2018.01); *G16H 50/20* (2018.01); *G16H 50/30* (2018.01); *A63B 2024/0065* (2013.01)

(58) Field of Classification Search
  CPC ...... G16H 50/20; G16H 50/30; A61B 5/6898; A61B 2503/10; A61B 2505/09; A61B 5/002; A61B 5/0022; A61B 5/7275; A61B 5/7465
  See application file for complete search history.

(56) References Cited

U.S. PATENT DOCUMENTS

| | | | |
|---|---|---|---|
| 2017/0050081 A1* | 2/2017 | Jones | A63F 13/795 |
| 2017/0228229 A1* | 8/2017 | Jain | H04L 67/01 |
| 2017/0287048 A1* | 10/2017 | Salomon | G06Q 30/0631 |
| 2017/0351388 A1* | 12/2017 | Grunewald | H04W 4/60 |
| 2017/0361164 A1* | 12/2017 | Rueckmann | G09B 19/0038 |
| 2018/0133552 A1 | 5/2018 | Jagroop et al. | |
| 2018/0264344 A1 | 9/2018 | Bollinger et al. | |
| 2019/0255384 A1* | 8/2019 | Bastide | A61B 5/0022 |

FOREIGN PATENT DOCUMENTS

| | | | |
|---|---|---|---|
| CN | 106021507 A | 10/2016 | |
| CN | 106063231 A | 10/2016 | |
| CN | 106530004 A | 3/2017 | |
| CN | 107357606 A | 11/2017 | |
| CN | 107506577 A | 12/2017 | |
| CN | 108133742 A | 6/2018 | |
| CN | 108319721 A | 7/2018 | |
| KR | 20160000124 A | 1/2016 | |
| WO | 2014017861 A1 | 1/2014 | |
| WO | WO-2014011858 A1 * | 1/2014 | ........... A61B 5/0022 |
| WO | WO-2018140653 A1 * | 8/2018 | ......... A63B 71/0622 |

OTHER PUBLICATIONS

Supplementary European Search Report issued in counterpart European Patent Application No. 19905906.4, dated Jan. 12, 2022.
International Search Report and Written Opinion in corresponding PCT Application No. PCT/CN2019/079992, dated May 31, 2019.
First Office Action issued in counterpart Chinese Patent Application No. 201811620014.8, dated Nov. 30, 2022.

\* cited by examiner

FITNESS MANAGEMENT METHOD, DEVICE, AND COMPUTER READABLE STORAGE MEDIUM

CROSS REFERENCE TO RELATED APPLICATIONS

The present application is the national stage of International Application No. PCT/CN2019/079992, filed on Mar. 28, 2019, which claims the benefit of Chinese patent application filed with the National Intellectual Property Administration on Dec. 27, 2018, with the application number 201811620014.8 and the title "FITNESS MANAGEMENT METHOD, DEVICE, AND COMPUTER READABLE STORAGE MEDIUM", the entire contents of which are hereby incorporated by reference.

TECHNICAL FIELD

The present application relates to the technical field of data processing, in particular to a fitness management method, a device and a computer readable storage medium.

BACKGROUND

Exercises help to shape a healthy and strong body and is one of the common ways for people to improve their physique. Among them, planned exercise trainings can achieve more with less effort. However, only a professional fitness coach can make a reasonable and appropriate training plan. It is too expensive to hire a personal coach. For some people who are not familiar with human bodies and training extreme intensity, they can only carry out imitation trainings through videos downloaded from the Internet or videos in some sport APPs.

However, in this kind of sports training mode, users are often required to actively select sport APPs or videos. The sport APPs or videos downloaded by the users may not aim at the health statuses of the users, resulting that the physical qualities of the users who exercise according to the sport APPs or videos cannot be reasonably improved.

The above content is only used to assist in understanding the technical solution of this application and does not mean that the above content is recognized as prior art.

SUMMARY

The main objective of the present application is to provide a fitness management method, a device and a computer readable storage medium, aiming to solve the technical problem that the sport APPs or videos downloaded by the users does not match the health statuses of the users.

In order to achieve the above objective, the present application provides a fitness management method applied to a smart terminal, wherein the fitness management method comprises the following operations:

obtaining a health evaluation result and health planning information corresponding to a first user account currently logged in;

generating a fitness project based on the health evaluation result and the health planning information;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

In addition, in order to achieve the above objective, the present application also provides a fitness management device comprising a memory, a processor, and computer readable instructions stored in the memory and executable by the processor, when the computer readable instructions are executed by the processor, the operations of the aforementioned fitness management method are realized.

In addition, in order to achieve the above objective, the present application also provides a computer readable storage medium in which computer readable instructions are stored, when the computer readable instructions are executed by a processor, the operations of the aforementioned fitness management method are realized.

The present application obtains the health evaluation result and health planning information corresponding to the first user account currently logged in; generates a fitness project based on the health evaluation result and the health planning information; determines whether the smart terminal is currently connected to a data network; determines whether there is a target network fitness application matching the fitness project among the network fitness applications currently installed in the smart terminal in response to a determination that the smart terminal is currently connected to the data network; and displays a first startup selection interface of the target network fitness application in response to a determination that there is a target network fitness application matching the fitness project. Furthermore, it can recommend a reasonable network fitness application to the user according to the user's health evaluation result and health planning information, avoid the situation that the user manually downloads and runs or starts the fitness application that does not match the user's health status, results in poor exercise effect, and improve the user experience.

The realization of purposes, functional characteristics and advantages of the present application will be further described in combination with the embodiments and with reference to the drawings.

DETAILED DESCRIPTION OF THE EMBODIMENTS

It should be understood that the specific embodiments described herein are only used to explain the present application only and are not intended to limit the present application.

Figure 1:
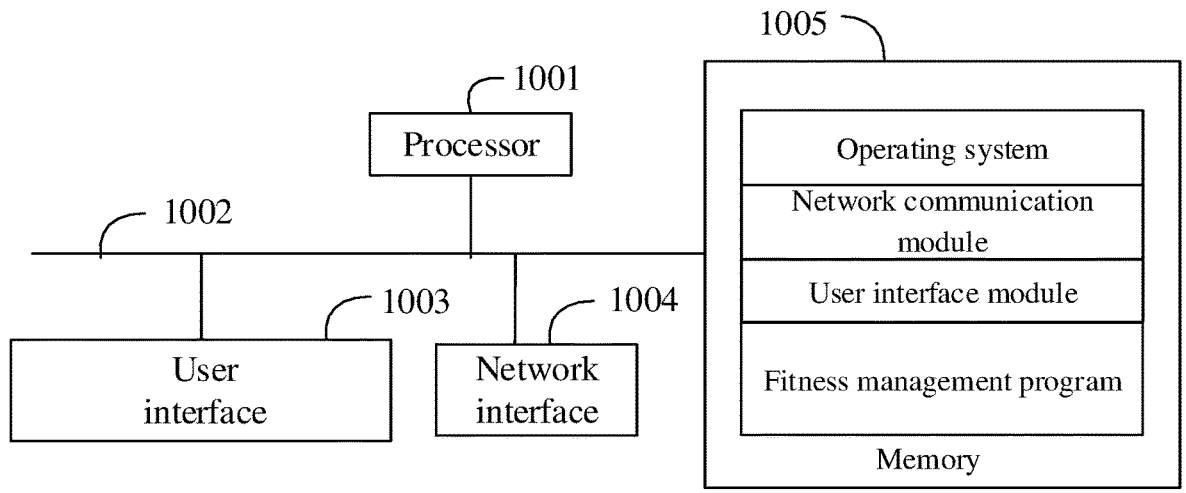
FIG. 1 is a schematic structural diagram of a fitness management device of a hardware operating environment involved in an embodiment of the present application.

As shown in FIG. 1, FIG. 1 is a schematic structural diagram of a fitness management device of a hardware operating environment involved in an embodiment of the present application.

The fitness management device of the embodiment of the present application can be a smart TV, a PC, a smart phone, a tablet computer, an electronic book reader, an MP3 (Moving Picture Experts Group Audio Layer III) player, an MP4 (Moving Picture Experts Group Audio Layer IV) player, a portable computer or another mobile terminal device with a display function.

As shown in FIG. 1, the fitness management device can include a processor 1001, such as a CPU, a network interface 1004, a user interface 1003, a memory 1005, and a communication bus 1002. Where, the communication bus 1002 is used to implement connection and communication between those components. The user interface 1003 can include a display screen, an input unit such as a Keyboard, and a user interface 1003 may optionally include a standard wired interface, and a wireless interface. The network interface 1004 may optionally include a standard wired interface, and a wireless interface (e.g., a WI-FI interface). The memory 1005 may be a high-speed RAM memory or a non-volatile memory, such as a magnetic disk memory. The memory 1005 may optionally be a storage device independent of the aforementioned processor 1001.

Optionally, the fitness management device may also include a camera, a RF (Radio Frequency) circuit, a sensor, an audio circuit, a WiFi module, and the like.

As will be appreciated by those skilled in that art, the structure of the fitness management device shown in FIG. 1 does not constitute a definition of the fitness management device and the fitness management device may include more or less components than shown, or a combination of certain components, or with different arrangements of components.

As shown in FIG. 1, the memory 1005, which is a computer storage medium, can include an operating system, a network communication module, a user interface module, and computer readable instructions.

In the fitness management device shown in FIG. 1, the network interface 1004 is mainly used for connecting a background server and performing data communication with the background server. The user interface 1003 is mainly used for connecting a client (user end) and performing data communication data with the client. The processor 1001 can be used to invoke the computer readable instructions stored in the memory 1005.

In this embodiment, the fitness management device includes the memory 1005, the processor 1001, and the computer readable instructions stored in the memory 1005 and executable by the processor 1001, where the processor 1001 invokes the computer readable instructions stored in the memory 1005 and performs the following operations:

obtaining a health evaluation result and health planning information corresponding to a first user account currently logged in;

generating a fitness project based on the health evaluation result and the health planning information;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

Further, the processor 1001 can invoke the computer readable instructions stored in the memory 1005 and perform the following operations:

in response to a determination that the smart terminal is not currently connected to the data network, determining whether there is a target local fitness application matching the fitness project among local fitness applications currently installed in the smart terminal;

in response to a determination that there exists the target local fitness application, displaying a second startup selection interface of the target local fitness application.

Further, the processor 1001 can invoke the computer readable instructions stored in the memory 1005 and perform the following operations:

in response to a determination that there is no target network fitness application matching the fitness project, acquiring a fitness video corresponding to the fitness project;

displaying a playing selection interface corresponding to the fitness video.

Further, the processor 1001 can invoke the computer readable instructions stored in the memory 1005 and perform the following operations:

detecting that a login operation corresponding to the first user account is completed, sending an acquisition request corresponding to the first user account to a cloud server for the cloud server to feed back historical health detection data and health planning information corresponding to the first user account based on the acquisition request;

displaying the historical health detection data and the health planning information after receiving the historical health detection data and the health planning information;

performing a health evaluation processing based on the historical health detection data to obtain the health evaluation result.

Further, the processor 1001 can invoke the computer readable instructions stored in the memory 1005 and perform the following operations:

during the smart terminal playing a video program, acquiring position information of a health acquisition device corresponding to the first user account in real time;

in response to a determination that a position change of the health acquisition device is less than a preset value based on the position information, determining whether a duration of the position change of the health acquisition device less than the preset value is greater than a preset duration;

in response to a determination that the duration of the position change of the health acquisition device less than the preset value is greater than the preset duration, outputting fitness reminding information, or sending the fitness reminding information to the health acquisition device.

Further, the processor 1001 can invoke the computer readable instructions stored in the memory 1005 and perform the following operations:

receiving a fitness request corresponding to the fitness reminding information, executing the operation of obtaining a health evaluation result and health planning information corresponding to a first user account currently logged in.

Further, the processor 1001 can invoke the computer readable instructions stored in the memory 1005 and perform the following operations:

in response to that registration of a second user account is completed, displaying a health acquisition device binding interface corresponding to the second user account;

in response to receiving a binding request triggered based on the health acquisition device binding interface, acquiring identification information of a health acquisition device corresponding to the binding request;

performing a binding operation of binding the second user account based on the identification information.

Figure 2:
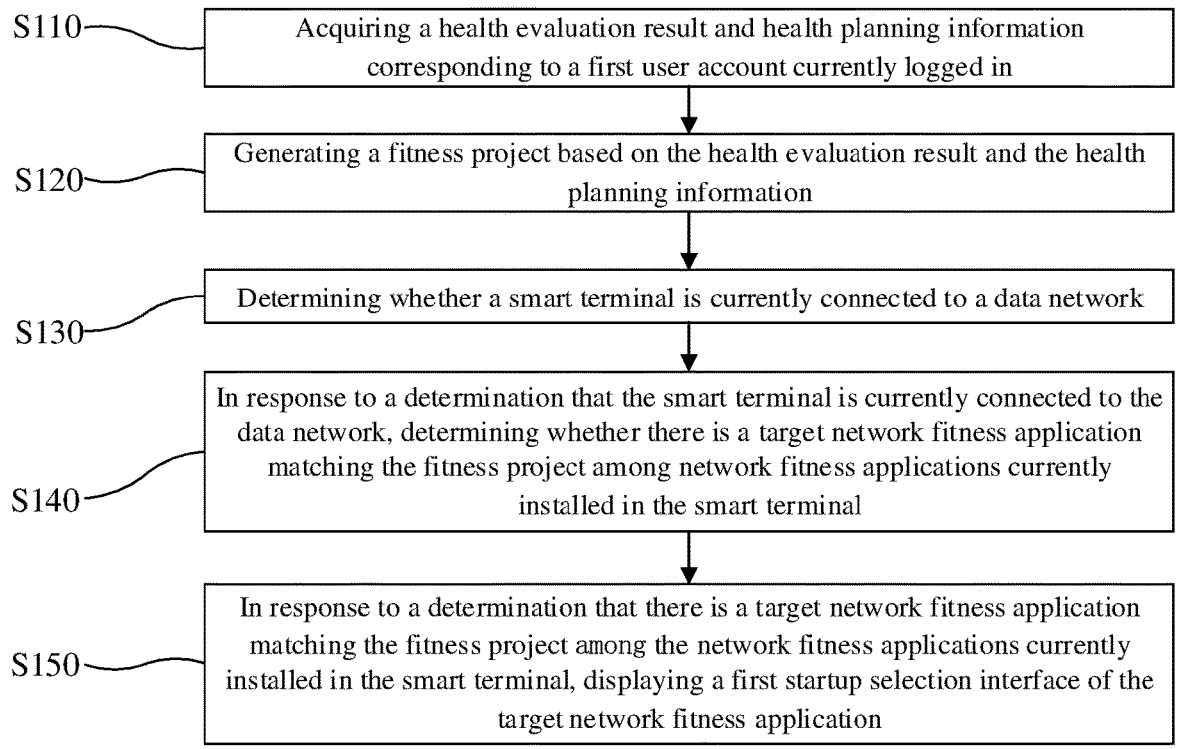
FIG. 2 is an illustrative flowchart of a first embodiment of a fitness management method of the present application.

The present application also provides a fitness management method. Referring to FIG. 2, FIG. 2 is an illustrative flowchart of a first embodiment of the fitness management method of the present application.

The fitness management method is applied to a smart terminal, which includes an intelligent equipment such as an intelligent TV, a mobile phone or the like.

The fitness management method comprises the following operations:

operation S110, acquiring a health evaluation result and health planning information corresponding to a first user account currently logged in.

In this embodiment, after a user logs in a user account, or, after the user logs in the user account and the user manually enters a health management interface corresponding to the first user account through a terminal such as a remote controller during a process of watching a video program, or, receiving a fitness request corresponding to fitness reminding information, the smart terminal obtains a health evaluation result and health planning information corresponding to the first user account currently logged in.

Specifically, the historical health detection data and the health planning information corresponding to the first user account can be stored in a preset storage area of the smart terminal or be stored in a cloud server. The smart terminal searches the preset storage area according to the user account. If the preset storage area currently stores the historical health detection data and the health planning information corresponding to the first user account, the historical health detection data and the health planning information corresponding to the first user account are obtained from the preset storage area, and a health evaluation processing is carried out based on the historical health detection data to obtain the health evaluation result. If there does not exist the historical health detection data and the health planning information corresponding to the first user account in the preset storage area, an acquisition request is sent to the cloud server based on the first user account, The cloud server feeds back the historical health detection data and the health planning information corresponding to the first user account according to the acquisition request. The smart terminal performs the health evaluation processing based on the historical health detection data to obtain the health evaluation result, or the cloud server performs the health evaluation processing based on the historical health detection data to obtain the health evaluation result, and feeds back the health evaluation result and the health planning information corresponding to the first user account.

Operation S120, generating a fitness project based on the health evaluation result and the health planning information.

In this embodiment, after the health evaluation result and the health planning information corresponding to the first user account is obtained, a fitness project is generated based on the health evaluation result and the health planning information. Specifically, the fitness project includes a type of exercise, a recommended exercise duration, and the like. For example, if the health evaluation result is obesity and the health planning information is that the user successfully lost weight for half a year, the fitness project includes exercises of a weight loss type, a recommended exercise duration for each day, and the like.

It should be noted that the fitness project may also include the health evaluation result and the dietary requirements corresponding to the health planning information.

Operation S130, determining whether a smart terminal is currently connected to a data network.

In this embodiment, when to determine the fitness project, it is determined whether the smart terminal is currently connected to a data network, where the data network may be a mobile data network or a WIFI network.

Operation S140, in response to a determination that the smart terminal is currently connected to the data network, determining whether there is a target network fitness application matching the fitness project among network fitness applications currently installed in the smart terminal.

In this embodiment, the smart terminal can currently be installed with network fitness applications that need to be connected to the network and local applications that does not need to be connected to the network. If the smart terminal is currently connected to the data network, it is determined whether there is a target network fitness application matching the fitness project among the network fitness applications currently installed in the smart terminal, for example, when the fitness project includes weight loss exercises, it is determined whether the smart terminal is currently installed with weight loss network fitness applications.

Operation S150, in response to a determination that there is a target network fitness application matching the fitness project among the network fitness applications currently installed in the smart terminal, displaying a first startup selection interface of the target network fitness application.

In this embodiment, if there is a target network fitness application matching the fitness project in the network fitness applications currently installed in the smart terminal, a first startup selection interface of the target network fitness application is displayed for the user to select whether to start the target network fitness application.

It should be noted that, the first startup selection interface may include an application startup icon of the target web fitness application. Moreover, if there are a plurality of target network fitness applications, the first startup selection interface includes application startup icons of the plurality of target network fitness applications, and the user can trigger a startup instruction of a target network fitness application through the application startup icon of the target network fitness application in the first startup selection interface.

Further, in one embodiment, the fitness management method further includes:

sending, by a health acquisition device, health detection data to the cloud server for the cloud server to update the historical health detection data of the user account corresponding to the health acquisition device based on the health detection data.

In this embodiment, when a user wears a health acquisition device, the health acquisition device can be started by a key of the health acquisition device. After the health acquisition device is started, the health acquisition device collects the health detection data of the user in real time, and sends the health detection data to the cloud server in real time or at regular intervals, and the cloud server updates the historical health detection data of a user account corresponding to the health acquisition device based on the health detection data.

The health acquisition device includes bracelets, wristbands, waistbands or other equipment.

The fitness management method provided in the embodiment obtains a health evaluation result and health planning information corresponding to the first user account currently logged in; generates a fitness project based on the health evaluation result and the health planning information; determines whether the smart terminal is currently connected to a data network; determines whether there is a target network fitness application matching the fitness project among network fitness applications currently installed in the smart terminal when the smart terminal is currently connected to the data network; and finally, displays a first startup selection interface of the target network fitness application in response to a determination that the target network fitness application matching the fitness project exists among the network fitness applications currently installed in the smart terminal. Furthermore, it can recommend a reasonable network fitness application to the user according to the user's health evaluation result and health planning information, thereby avoiding the situation that the user manually downloads, runs or starts fitness applications that do not match the user's health status and results in poor exercise effect, and improving the user experience.

Figure 3:
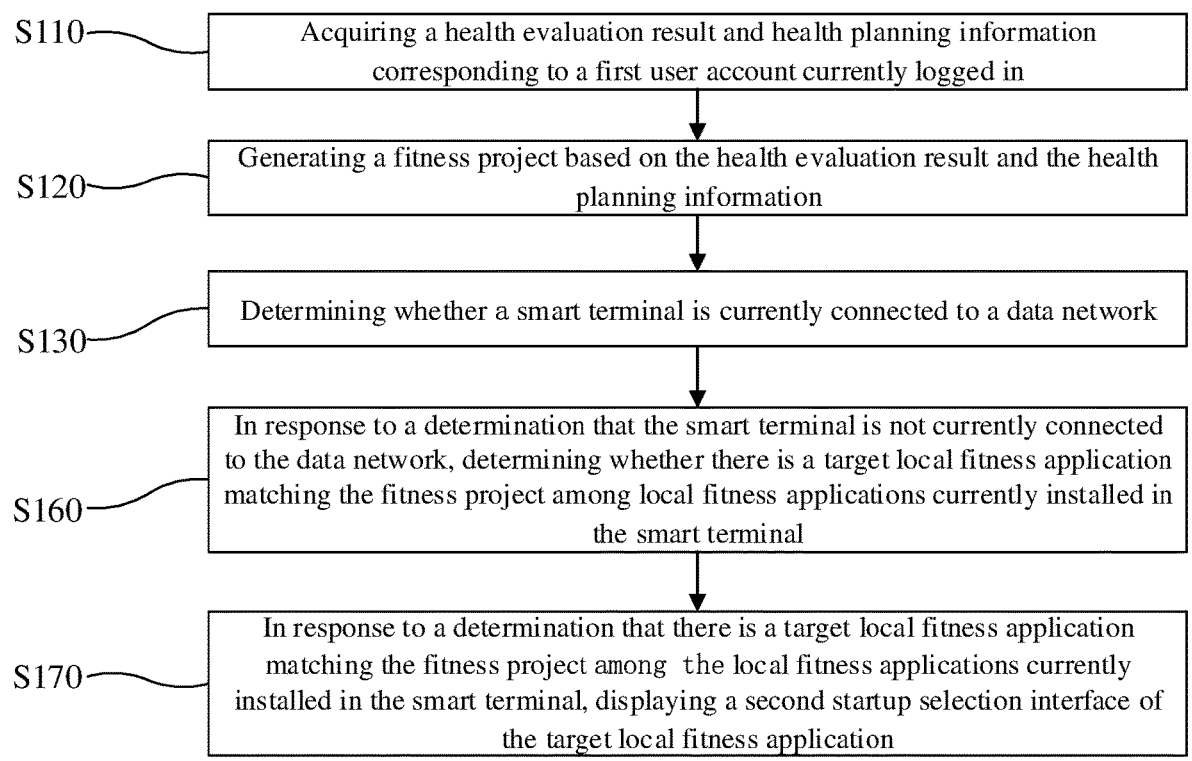
FIG. 3 is an illustrative flowchart of a second embodiment of the fitness management method of the present application.

Based on the first embodiment, a second embodiment of the fitness management method of the present application is provided. Referring to FIG. 3, in the present embodiment, after operation S130, the fitness management method further includes:

operation S160, in response to a determination that the smart terminal is not currently connected to the data network, determining whether there is a target local fitness application matching the fitness project among local fitness applications currently installed in the smart terminal;

operation S170, in response to a determination that there is a target local fitness application matching the fitness project among the local fitness applications currently installed in the smart terminal, displaying a second startup selection interface of the target local fitness application.

In this embodiment, the smart terminal is currently installed with local applications that do not need to be connected to the network. In response to a determination that the smart terminal is not currently connected to the data network, it is determined whether there is a target local fitness application matching the fitness project among the local fitness applications currently installed in the smart terminal. For example, when the fitness project includes weight loss exercises, it is determined whether the smart terminal is currently installed with weight loss local fitness applications.

In this embodiment, in response to a determination that there is a target local fitness application matching the fitness project among the local fitness applications currently installed in the smart terminal, a second startup selection interface of the target local fitness application is displayed for the user to select whether to start the target local fitness application.

It should be noted that, the second startup selection interface can include an application startup icon of the target local fitness application, Moreover, if there are a plurality of target local fitness applications, the second startup selection interface includes application startup icons of the plurality of target local fitness applications, and the user can trigger a startup instruction of a target local fitness application through the application startup icon of the target local fitness application in the second startup selection interface.

The fitness management method provided by the embodiment determines whether there is a target local fitness application matching the fitness project among the local fitness applications currently installed in the smart terminal when the smart terminal is not currently connected to the data network; displays a second startup selection interface of the target local fitness application in response to a determination that the target local fitness application matching the fitness project exists among the local fitness applications currently installed in the smart terminal. When the smart terminal is not currently connected to the data network, a reasonable local fitness application can be recommended to the user according to the user's health evaluation result and health planning information, thereby avoiding the situation that the user manually downloads, runs or starts fitness applications that do not match the user's health status and results in poor exercise effect, and improving the user experience.

Figure 4:
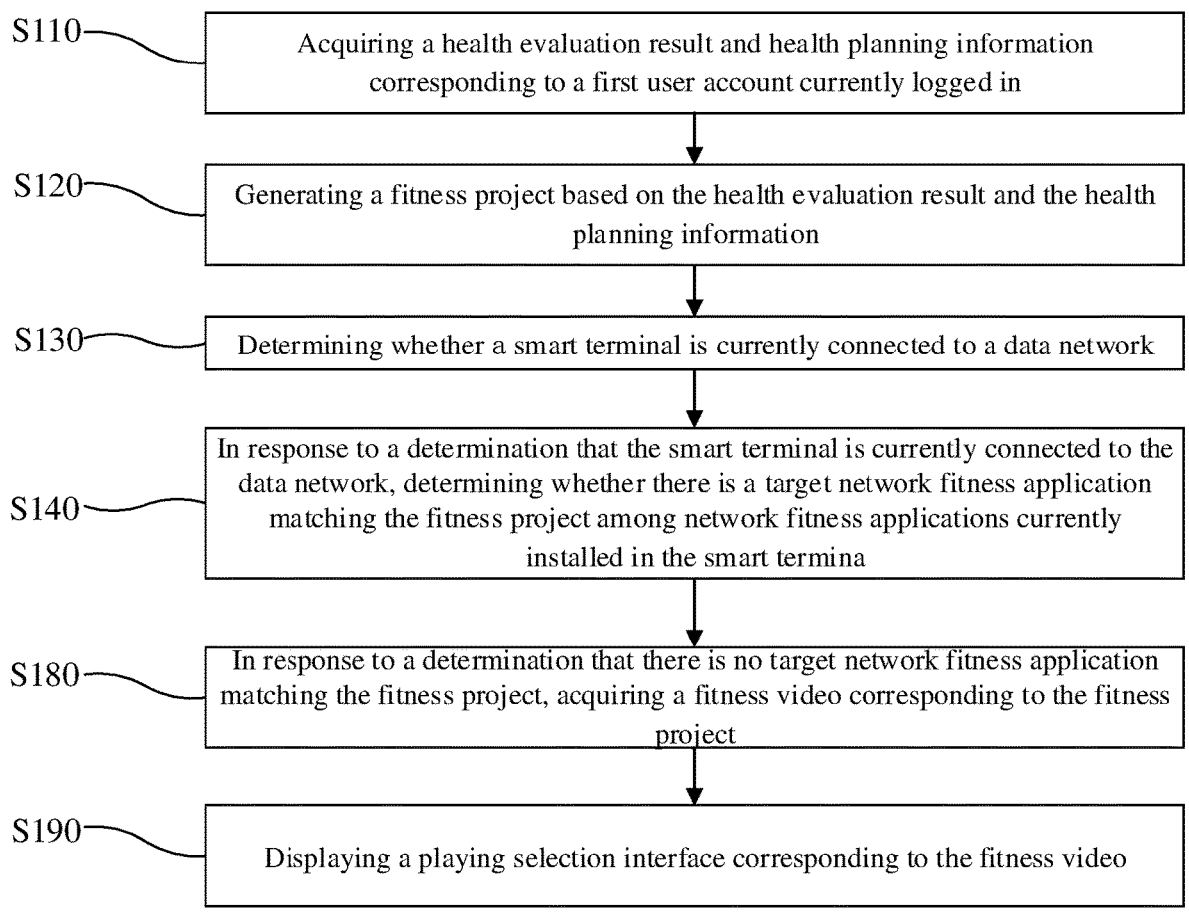
FIG. 4 is an illustrative flowchart of a third embodiment of the fitness management method of the present application.

Based on the first embodiment, a third embodiment of the fitness management method of the present application is provided. Referring to FIG. 4, in this embodiment, after operation S140, the fitness management method further includes:

operation S180, in response to a determination that there is no target network fitness application matching the fitness project, acquiring a fitness video corresponding to the fitness project;

operation S190, displaying a playing selection interface corresponding to the fitness video.

In this embodiment, if there is no target network fitness application matching the fitness project among the network fitness applications currently installed in the smart terminal, a fitness video corresponding to the fitness project is obtained, specifically, a network search can be carried out according to the type of exercises of the fitness project to obtain a fitness video related to the type of exercises, and then a playing selection interface corresponding to the fitness video is displayed.

The playback selection interface may include a playback icon of the fitness video, and if there are a plurality of fitness videos, the playback selection interface includes playback icons of the plurality of fitness videos, and the user can trigger a playback instruction of a fitness video through the playback icon of the fitness video in the playback selection interface.

According to the fitness management method provided by the embodiment, if there is no target network fitness application matching the fitness project, a fitness video corresponding to the fitness project is obtained; a playing selection interface corresponding to the fitness video is displayed, furthermore, when the network fitness application corresponding to the fitness project is not installed in the smart terminal, a reasonable fitness video is recommended to the user according to the user's health evaluation result and health planning information, thereby avoiding the situation that the user manually plays fitness videos that do not match the user's health status and leads to poor exercise effect, and improving the user experience.

Figure 5:
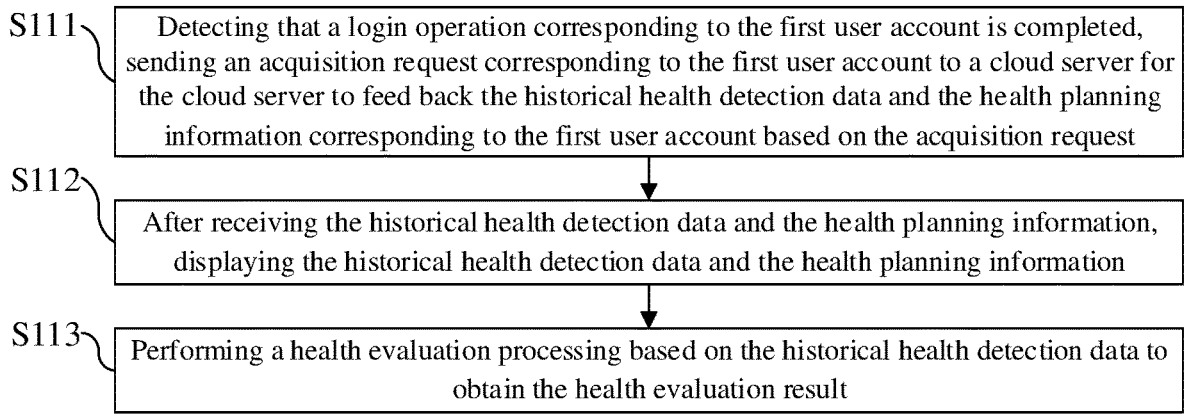
FIG. 5 is a detailed illustrative flowchart of operations of acquiring a health evaluation result and health planning information corresponding to a first user account currently logged in in a fourth embodiment of the fitness management method of the present application.

Based on the first embodiment, a fourth embodiment of the fitness management method of the present application is presented. Referring to FIG. 5, in the present embodiment, operation S110 includes:

S111, detecting that a login operation corresponding to the first user account is completed, sending an acquisition request corresponding to the first user account to a cloud server for the cloud server to feed back the historical health detection data and the health planning information corresponding to the first user account based on the acquisition request;

operation S112, after receiving the historical health detection data and the health planning information, displaying the historical health detection data and the health planning information;

operation S113, performing a health evaluation processing based on the historical health detection data to obtain the health evaluation result.

In this embodiment, the smart terminal does not store the historical health detection data and the health planning information corresponding to the first user account. When detecting that a login operation corresponding to the first user account is completed, the smart terminal sends an acquisition request to a cloud server based on the first user account, and the cloud server feeds back the historical health detection data and the health planning information corresponding to the first user account according to the acquisition request. After receiving the historical health detection data and the health planning information, the smart terminal displays the historical health detection data and the health planning information, and performs a health evaluation processing based on the historical health detection data to obtain the health evaluation result.

It should be noted that, when the historical health detection data and the health planning information are displayed, the user can reset the health planning information. Specifically, the user may trigger a reset instruction of the health planning information by operating a display interface of the historical health detection data and the health planning information. After receiving the reset instruction, a setting interface of the health planning information is displayed, and after receiving a setting completion instruction triggered based on the setting interface, the health planning information reset by the user is obtained according to the setting completion instruction.

The fitness management method provided in this embodiment detects that a login operation corresponding to the first user account is completed, sends an acquisition request corresponding to the first user account to a cloud server for the cloud server to feed back historical health detection data and health planning information corresponding to the first user account based on the acquisition request; displays the historical health detection data and the health planning information after receiving the historical health detection data and the health planning information; and carries out a health evaluation processing based on the historical health detection data to obtain the health evaluation result, so that the smart terminal can obtain the historical health detection data and the health planning information through the server, and reduces a occupied data storage of the smart terminal.

Figure 6:
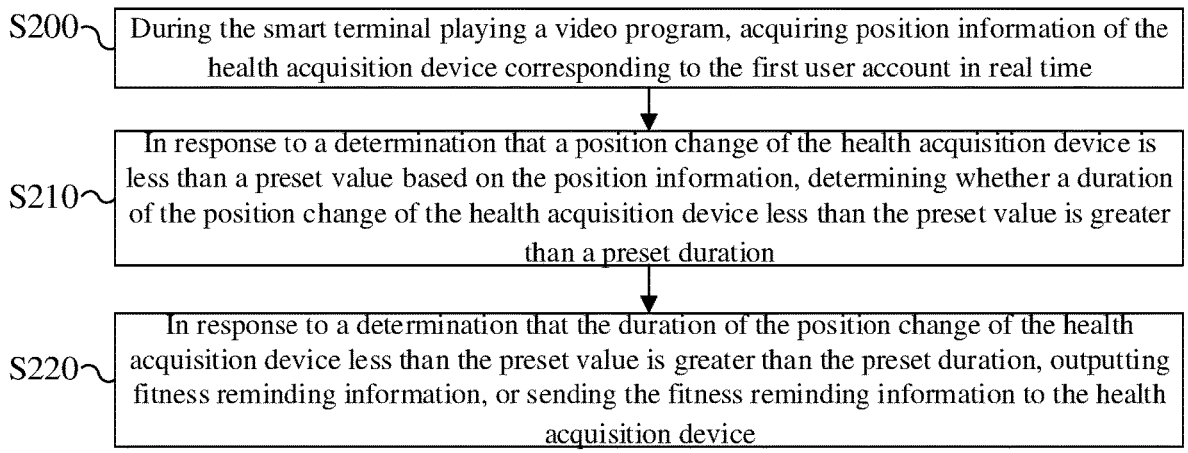
FIG. 6 is an illustrative flowchart of a fifth embodiment of the fitness management method of the present application.

Based on the first embodiment, a fifth embodiment of the fitness management method of the present application is provided. Referring to FIG. 6, in the present embodiment, the fitness management method further includes:

operation S200, during the smart terminal playing a video program, acquiring position information of the health acquisition device corresponding to the first user account in real time;

operation S210, in response to a determination that a position change of the health acquisition device is less than a preset value based on the position information, determining whether a duration of the position change of the health acquisition device less than the preset value is greater than a preset duration;

operation S220, in response to a determination that the duration of the position change of the health acquisition device less than the preset value is greater than the preset duration, outputting fitness reminding information, or sending the fitness reminding information to the health acquisition device.

In this embodiment, after the login operation corresponding to the first user account is completed, if the user watches a video program with the smart terminal, and the video program does not include fitness videos, position information of the health acquisition device corresponding to the first user account is obtained in real time, a position change of the health acquisition device is determined whether to be less than a preset value based on the position information. Specifically, it is judged whether a moving distance of the health acquisition device is less than the preset value. When it is determined that the position change of the health acquisition device is less than the preset value based on the position information, it is determined whether a duration of the position change of the health acquisition device less than the preset value is greater than a preset duration, that is, it is judged whether the health acquisition device is in a fixed preset area within a time length greater than the preset duration. If yes, it indicates that the user is watching the video program for a long time and is not moving (or only moving in a small area). Therefore, fitness reminding information is output or sent to the health acquisition device, so that the user can exercise in time and the health of the user is not affected due to the fact of watching a video program for a long time and not moving.

The preset value can be reasonably set, for example, the preset value is 10 CM.

Further, in one embodiment, after operation S220, the fitness management method further comprises:

receiving a fitness request corresponding to the fitness reminding information, executing the operation of obtaining a health evaluation result and health planning information corresponding to a first user account currently logged in.

In this embodiment, if the smart terminal outputs fitness reminding information, the user can trigger a fitness request according to the fitness reminding information through a remote controller or another equipment. If the fitness reminding information is sent to the health acquisition device, and the health acquisition device displays the fitness reminding information, the user can trigger the fitness request according to the fitness reminding information with the health acquisition device. The health acquisition device sends the fitness request to the smart terminal. After receiving the fitness request corresponding to the fitness reminding information, the operation of obtaining a health evaluation result and health planning information corresponding to a first user account currently logged in is executed.

According to the fitness management method provided by this embodiment, when the smart terminal plays a video program, position information of the health acquisition device corresponding to the first user account is obtained in real time; when determining that a position change of the health acquisition device is less than a preset value based on the position information, whether a duration of the position change of the health acquisition device less than the preset value is greater than the preset duration is determined; if yes, fitness reminding information is output or sent to the health acquisition device, so that the user can exercise timely according to the fitness reminding information, the effect on the health of the user due to long time watching a video program without moving is avoided, and the user experience is improved.

Figure 7:
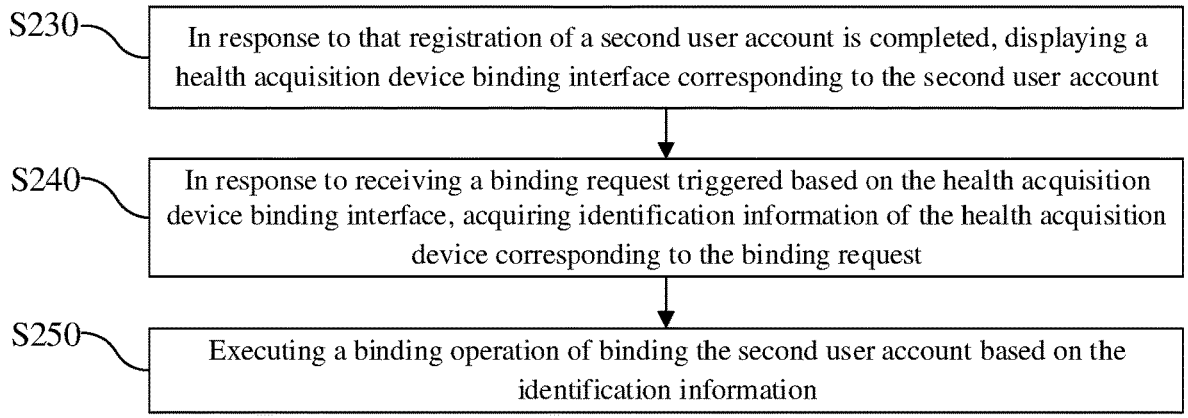
FIG. 7 is an illustrative flowchart of a sixth embodiment of the fitness management method of the present application.

Based on the first embodiment, a sixth embodiment of the fitness management method of the present application is provided. Referring to FIG. 7, in the present embodiment, the fitness management method further comprises:

Operation S230, in response to that registration of a second user account is completed, displaying a health acquisition device binding interface corresponding to the second user account;

Operation S240, in response to receiving a binding request triggered based on the health acquisition device binding interface, acquiring identification information of the health acquisition device corresponding to the binding request;

Operation S250, executing a binding operation of binding the second user account based on the identification information.

In this embodiment, users can register user accounts. After the completion of registration of a second user account, a management interface of the second user account is entered, and a health acquisition device binding interface corresponding to the second user account is displayed. The user can input identification information of a health acquisition device in the health acquisition device binding interface. When receiving a binding request triggered on the health acquisition device binding interface, the identification information of the health acquisition device corresponding to the binding request is obtained, and a binding operation of binding the second user account based on the identification information is executed, thus realizing a binding of a health acquisition device with a user account.

The fitness management method provided in this embodiment. after registration of a second user account is completed, a health acquisition device binding interface corresponding to the second user account is displayed. At the time of receiving a binding request triggered based on the health acquisition device binding interface, identification information of the health acquisition device corresponding to the binding request is obtained, and a binding operation of binding the second user account based on the identification information is executed, thereby realizing a binding of a health acquisition device with a user account, facilitating accurate collections of health detection data, and improving the user experience.

In addition, embodiments of the present application also provides a computer readable storage medium in which computer readable instructions are stored that, when the computer readable instructions are executed by a processor, the following operations are carried out:

obtaining a health evaluation result and health planning information corresponding to a first user account currently logged in;

generating a fitness project based on the health evaluation result and the health planning information;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

Further, when the computer readable instructions are executed by the processor, the following operations are also carried out:

in response to a determination that the smart terminal is not currently connected to the data network, determining whether there is a target local fitness application matching the fitness project among local fitness applications currently installed in the smart terminal;

in response to a determination that there exists the target local fitness application, displaying a second startup selection interface of the target local fitness application.

Further, when the computer readable instructions are executed by the processor, the following operations are also carried out:

in response to a determination that there is no target network fitness application matching the fitness project, acquiring a fitness video corresponding to the fitness project;

displaying a playing selection interface corresponding to the fitness video.

Further, when the computer readable instructions are executed by the processor, the following operations are also carried out:

detecting that a login operation corresponding to the first user account is completed, sending an acquisition request corresponding to the first user account to a cloud server for the cloud server to feed back historical health detection data and health planning information corresponding to the first user account based on the acquisition request;

displaying the historical health detection data and the health planning information after receiving the historical health detection data and the health planning information;

performing a health evaluation processing based on the historical health detection data to obtain the health evaluation result.

Further, when the computer readable instructions are executed by the processor, the following operations are also carried out:

during the smart terminal playing a video program, acquiring position information of a health acquisition device corresponding to the first user account in real time;

in response to a determination that a position change of the health acquisition device is less than a preset value based on the position information, determining whether a duration of the position change of the health acquisition device less than the preset value is greater than a preset duration;

in response to a determination that the duration of the position change of the health acquisition device less than the preset value is greater than the preset duration, outputting fitness reminding information, or sending the fitness reminding information to the health acquisition device.

Further, when the computer readable instructions are executed by the processor, the following operations are also carried out:

receiving a fitness request corresponding to the fitness reminding information, executing the operation of obtaining a health evaluation result and health planning information corresponding to a first user account currently logged in.

Further, when the computer readable instructions are executed by the processor, the following operations are also carried out:

in response to that registration of a second user account is completed, displaying a health acquisition device binding interface corresponding to the second user account;

in response to receiving a binding request triggered based on the health acquisition device binding interface, acquiring identification information of a health acquisition device corresponding to the binding request;

performing a binding operation of binding the second user account based on the identification information.

It should be noted that in this document, the terms "include", "comprise" or any other variant thereof are intended to cover a non-exclusive inclusion. Thus, a process, method, article, or system that includes a series of elements not only includes those elements, but also includes other elements that are not explicitly listed, or also includes elements inherent to the process, method, article, or system. If there are no more restrictions, the element defined by the sentence "including a . . . " does not exclude the existence of other identical elements in the process, method, article or system that includes the element.

The serial numbers of the foregoing embodiments of the present disclosure are only for description, and do not represent the advantages and disadvantages of the embodiments.

Through the description of the above embodiments, those skilled in the art can clearly understand that the methods in the above embodiments can be implemented by means of software plus a necessary general hardware platform, and of course, can also be implemented by hardware, but in many cases the former is better. Based on this understanding, the technical solution of the present invention can be embodied in the form of a software product in essence or part that contributes to the existing technology, and the computer software product is stored in a storage medium (such as a ROM/RAM, a magnetic disk, an optical disk) as described above, and includes instructions to enable a terminal (which can be a mobile phone, a computer, a server, a network device, or the like) to execute the methods described in various embodiments of the present invention.

The above are only preferred embodiments of the present application and is not thus to limit a scope of the present application. Any equivalent structure or equivalent process transformation made based on the contents of the specification and the drawings of the present application, or directly or indirectly applied to other related technical fields, are all included in the scope of the present application.

What is claimed is:

1. A fitness management method applied to a smart terminal, wherein the fitness management method comprises the following operations:

obtaining a health evaluation result and health planning information corresponding to a first user account currently logged in, wherein a health evaluation processing is carried out based on historical health detection data corresponding to the first user account to obtain the health evaluation result;

generating a fitness project based on the health evaluation result and the health planning information, wherein in response to a determination that the health evaluation result is obesity and the health planning information is that a user successfully lost weight for half a year, the fitness project comprises exercises of a weight loss type, and a recommended exercise duration for each day;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

2. The fitness management method as claimed in claim 1, wherein, after the operation of determining whether a smart terminal is currently connected to a data network, the fitness management method further comprises:

in response to a determination that the smart terminal is not currently connected to the data network, determining whether there is a target local fitness application matching the fitness project among local fitness applications currently installed in the smart terminal;

in response to a determination that there exists the target local fitness application, displaying a second startup selection interface of the target local fitness application.

3. The fitness management method as claimed in claim 1, wherein, after the operation of determining whether there is a target network fitness application matching the fitness project among network fitness applications currently installed in the smart terminal, the fitness management method further comprises:

in response to a determination that there is no target network fitness application matching the fitness project, acquiring a fitness video corresponding to the fitness project;

displaying a playing selection interface corresponding to the fitness video.

4. The fitness management method as claimed in claim 1, wherein the operation of obtaining a health evaluation result and health planning information corresponding to a first user account currently logged in comprises:

detecting that a login operation corresponding to the first user account is completed, sending an acquisition request corresponding to the first user account to a cloud server for the cloud server to feed back historical health detection data and health planning information corresponding to the first user account based on the acquisition request;

displaying the historical health detection data and the health planning information after receiving the historical health detection data and the health planning information;

performing a health evaluation processing based on the historical health detection data to obtain the health evaluation result.

5. The fitness management method as claimed in claim 1, further comprising:

during the smart terminal playing a video program, acquiring position information of a health acquisition device corresponding to the first user account in real time;

in response to a determination that a position change of the health acquisition device is less than a preset value based on the position information, determining whether a duration of the position change of the health acquisition device less than the preset value is greater than a preset duration;

in response to a determination that the duration of the position change of the health acquisition device less than the preset value is greater than the preset duration, outputting fitness reminding information, or sending the fitness reminding information to the health acquisition device.

6. The fitness management method as claimed in claim 5, wherein, after the operation of outputting fitness reminding information or sending the fitness reminding information to the health acquisition device, the fitness management method further comprises:

receiving a fitness request corresponding to the fitness reminding information, executing the operation of obtaining a health evaluation result and health planning information corresponding to a first user account currently logged in.

7. The fitness management method as claimed in claim 1, further comprising:

in response to that registration of a second user account is completed, displaying a health acquisition device binding interface corresponding to the second user account;

in response to receiving a binding request triggered based on the health acquisition device binding interface, acquiring identification information of a health acquisition device corresponding to the binding request;

performing a binding operation of binding the second user account based on the identification information.

8. The fitness management method as claimed in claim 1, further comprising:

sending, by a health acquisition device, health detection data to a cloud server for the cloud server to update the historical health detection data of the first user account corresponding to the health acquisition device based on the health detection data.

9. A fitness management device comprising a memory, a processor and computer readable instructions stored in the memory and executable on the processor, when the computer readable instructions are executed by the processor, the following operations are realized:

obtaining a health evaluation result and health planning information corresponding to a first user account currently logged in, wherein a health evaluation processing is carried out based on historical health detection data corresponding to the first user account to obtain the health evaluation result;

generating a fitness project based on the health evaluation result and the health planning information, wherein if the health evaluation result is obesity and the health planning information is that a user successfully lost weight for half a year, the fitness project comprises exercises of a weight loss type, and a recommended exercise duration for each day;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

10. The fitness management device as claimed in claim 9, wherein, after the operation of determining whether a smart terminal is currently connected to a data network, when the computer readable instructions are executed by the processor, the following operations are further realized:

in response to a determination that the smart terminal is not currently connected to the data network, determining whether there is a target local fitness application matching the fitness project among local fitness applications currently installed in the smart terminal;

in response to a determination that there exists the target local fitness application, displaying a second startup selection interface of the target local fitness application.

11. The fitness management device according to claim 9, wherein the operation of obtaining a health evaluation result and health planning information corresponding to a first user account currently logged in comprises:

detecting that a login operation corresponding to the first user account is completed, sending an acquisition request corresponding to the first user account to a cloud server for the cloud server to feed back historical health detection data and health planning information corresponding to the first user account based on the acquisition request;

displaying the historical health detection data and the health planning information after receiving the historical health detection data and the health planning information;

performing a health evaluation processing based on the historical health detection data to obtain the health evaluation result.

12. The fitness management device as claimed in claim 9, wherein when the computer readable instructions are executed by the processor, the following operations are further realized:

during the smart terminal playing a video program, acquiring position information of a health acquisition device corresponding to the first user account in real time;

in response to a determination that a position change of the health acquisition device is less than a preset value based on the position information, determining whether a duration of the position change of the health acquisition device less than the preset value is greater than a preset duration;

in response to a determination that the duration of the position change of the health acquisition device less than the preset value is greater than the preset duration, outputting fitness reminding information, or sending the fitness reminding information to the health acquisition device.

13. A computer readable storage medium, wherein computer readable instructions are stored in the computer readable storage medium, when the computer readable instructions are executed by a processor, the following operations are realized:

obtaining a health evaluation result and health planning information corresponding to a first user account currently logged in, wherein a health evaluation processing is carried out based on historical health detection data corresponding to the first user account to obtain the health evaluation result;

generating a fitness project based on the health evaluation result and the health planning information, wherein if the health evaluation result is obesity and the health planning information is that a user successfully lost weight for half a year, the fitness project comprises exercises of a weight loss type, and a recommended exercise duration for each day;

determining whether a smart terminal is currently connected to a data network;

in response to a determination that the smart terminal is currently connected to the data network, determining whether there is a target network fitness application matching the fitness project among network fitness applications currently installed in the smart terminal;

in response to a determination that there is the target network fitness application, displaying a first startup selection interface of the target network fitness application.

14. The computer readable storage medium as claimed in claim 13, wherein the operation of obtaining a health evaluation result and health planning information corresponding to a first user account currently logged in comprises:

detecting that a login operation corresponding to the first user account is completed, sending an acquisition request corresponding to the first user account to a cloud server for the cloud server to feed back historical health detection data and health planning information corresponding to the first user account based on the acquisition request;

displaying the historical health detection data and the health planning information after receiving the historical health detection data and the health planning information;

performing a health evaluation processing based on the historical health detection data to obtain the health evaluation result.

15. The computer readable storage medium as claimed in claim 13, wherein when the computer readable instructions are executed by the processor, the following operations are further realized:

during the smart terminal playing a video program, acquiring position information of a health acquisition device corresponding to the first user account in real time;

in response to a determination that a position change of the health acquisition device is less than a preset value based on the position information, determining whether a duration of the position change of the health acquisition device less than the preset value is greater than a preset duration;

in response to a determination that the duration of the position change of the health acquisition device less than the preset value is greater than the preset duration, outputting fitness reminding information, or sending the fitness reminding information to the health acquisition device.

* * * * *